United States Patent [19]

Takagawa et al.

[11] Patent Number: 6,072,098
[45] Date of Patent: *Jun. 6, 2000

[54] PROCESS FOR PRODUCING HIGHLY PURE 2,6-DIMETHYLNAPHTHALENE

[75] Inventors: Makoto Takagawa; Ryusuke Shigematsu, both of Tsukuba, Japan

[73] Assignee: Mitsubishi Gas Chemical Company, Inc., Tokyo, Japan

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/777,077

[22] Filed: Dec. 30, 1996

[30] Foreign Application Priority Data

Mar. 15, 1996 [JP] Japan .................................. 8-059740

[51] Int. Cl.[7] ................................ C07C 7/14; C07C 5/22
[52] U.S. Cl. ...................... 585/817; 585/816; 585/814; 585/479; 585/812; 585/481; 585/478
[58] Field of Search ...................... 585/477, 478, 585/479, 480, 481, 812, 813, 814, 816, 817

[56] References Cited

U.S. PATENT DOCUMENTS

| | | |
|---|---|---|
| 3,173,960 | 3/1965 | Robinson . |
| 3,590,091 | 6/1971 | Skarada et al. .......................... 260/674 |
| 3,649,708 | 3/1972 | Schroeder et al. .................. 260/674 N |
| 3,888,938 | 6/1975 | Ogasawara et al. ................. 260/668 A |
| 3,957,896 | 5/1976 | Yokoyama et al. .................. 260/668 A |
| 4,900,717 | 2/1990 | Holtmann et al. ....................... 585/812 |

FOREIGN PATENT DOCUMENTS 0 618 180  10/1994  European Pat. Off. .

OTHER PUBLICATIONS

Chemical Abstracts, vol. 84, No. 9, Mar. 1, 1976, Columbus, Ohio, Abstract No. 59048j, p. 482 of JP 50 108 247 A (TEIJIN) Aug. 26, 1975.

*Primary Examiner*—Walter D. Griffin
*Assistant Examiner*—Thuan D. Dang
*Attorney, Agent, or Firm*—Frishauf, Holtz, Goodman, Langer & Chick, P.C.

[57] ABSTRACT

There are disclosed an industrially advantageous process for efficiently producing highly pure 2,6-dimethylnaphthalene (DMN) in high yield from a mixture of DMN by carrying out in turn, the steps of isomerizing a mixture of DMN in the presence of a catalyst; crystallizing the isomerization reaction product in the presence of a solvent (e.g. an aliphatic or alicyclic saturated hydrocarbon) to precipitate 2,6-DMN crystal; isolating and recovering the 2,6-DMN thus precipitated; and distilling the mother liquor formed after the isolation of the crystal to obtain DMN fraction by removing the components having a higher boiling point than DMN and the components having a lower boiling point than DMN, while at least part of the DMN fraction is returned to the isomerization step and circulated through the process; a process for producing a 2,6-naphthalenedicarboxylic acid by subjecting the 2,6-DMN obtained by the above process to liquid-phase oxidation; and a process for producing 2,6-naphthalenedicarboxylic acid ester by esterifying 2,6-naphthalenedicarboxylic acid thus produced.

10 Claims, 1 Drawing Sheet

PROCESS FOR PRODUCING HIGHLY PURE 2,6-DIMETHYLNAPHTHALENE

BACKGROUND OF THE INVENTION

1. Field of the Invention

The present invention relates to a process for producing highly pure 2,6-dimethylnaphthalene. More particularly, it pertains to a process for efficiently producing, in high yield in an industrially advantageous manner, highly pure 2,6-dimethylnaphthalene useful as a starting raw material for a 2,6-naphthalenedicarboxylic acid from the mixture of dimethylnaphthalenes comprising as a principal component, 1,5-dimethylnaphthalene obtained preferably from o-xylene and butadiene as starting raw materials.

2. Description of the Related Arts

It has heretofore been known that a 2,6-naphthalenedicarboxylic acid and an ester thereof are each a compound of industrial importance as a starting raw material for a high performance polyester which is employed for the production of polyethylene naphthalate in the form of fiber, film and the like that is excellent in tensile strength and heat resistance.

The 2,6-naphthalenedicarboxylic acid and an ester thereof that are used for such a purpose are required to be highly pure and besides 2,6-dimethylnaphthalene (hereinafter dimethylnaphthalene is sometimes abbreviated to "DMN") which is used as a starting raw material thereof is required to be also highly pure because of the reasons described hereunder.

Specifically, 2,6-DMN, when being low in purity, causes the impurities contained therein to be oxidized or esterified, and eventually lowers the purity of a 2,6-naphthalenedicarboxylic acid and an ester thereof when being produced therefrom. A part of the impurities that are formed during the steps of oxidation and esterification, originating from the impurities in 2,6-DMN is extremely difficult to remove, thereby making it also extremely difficult to obtain a 2,6-naphthalenedicarboxylic acid or a dimethyl 2,6-naphthalenedicarboxylate each having high purity. In addition, such impurities, when being present in 2,6-DMN, deteriorates not only the purity of the above-mentioned acid and ester, but also the yield thereof based on 2,6-DMN to a remarkable extent. It is therefore, indispensable that highly pure 2,6-DMN be obtained in order to produce a 2,6-naphthalenedicarboxylic acid and a dimethyl 2,6-naphthalenedicarboxylate under industrially advantageous conditions. DMN has 10 isomers according to the positions of two methyl groups. Accordingly, 2,6-DMN as a starting raw material for a 2,6-naphthalenedicarboxylic acid is required to be a highly pure product substantially free from any of the isomers other than 2,6-DMN.

As the process for producing 2,6-DMN, there are available for example, a process in which 2,6-DMN is isolated from a tar fraction or a petroleum fraction, a process in which naphthalene or methylnaphthalene is methylated, succeedingly isomerized and separated and the like processes. Since the fractions and isomerization reaction products contain almost all of the 10 kinds of isomers, 2,6-DMN needs to be isolated from the mixture of a lot of isomers.

On the other hand, Japanese Patent Application Laid-Open Nos. 134634/1974, 8935/1975, 76852/1973 and 129534/1975 disclose a process for producing o-tolylpentene-2 in high yield from o-xylene and butadiene; a process for producing 1,5-dimethyltetralin by cyclizing o-tolylpentene-2; a process for producing 1,5-DMN in high yield and in high selectivity by dehydrogenating 1,5-dimethyltetralin; and a process for producing a mixture of isomers consisting essentially of 1,5-, 1,6- and 2,6-DMNs by isomerizing 1,5-DMN. Accordingly, by combining the above-mentioned processes it is made possible to produce a mixture of isomers consisting essentially of 1,5-, 1,6- and 2,6-DMNs from o-xylene and butadiene. Thus, there is made available a process for producing 2,6-DMN by isolating 2,6-DMN from the aforesaid mixture.

As described hereinbefore, any of the processes for producing 2,6-DMN that have heretofore been available makes it necessary to isolate 2,6-DMN from the mixture of isomers to recovery the same. However, it is extremely difficult to purify 2,6-DMN by means of distillation which is frequently applied to the separation and purification of ordinary organic compounds, since 10 kinds of isomers have each a boiling point very close to one another as shown hereunder together with the melting point.

|         | Boiling point (° C.) | Melting point (° C.) |
|---------|----------------------|----------------------|
| 1,5-DMN | 269                  | 82                   |
| 1,6-DMN | 266                  | −16                  |
| 2,6-DMN | 262                  | 112                  |
| 1,7-DMN | 263                  | −14                  |
| 1,8-DMN | 270                  | 65                   |
| 2,7-DMN | 262                  | 98                   |
| 1,3-DMN | 265                  | −4.2                 |
| 1,4-DMN | 265                  | 6                    |
| 2,3-DMN | 269                  | 104                  |
| 1,2-DMN | 271                  | −3.5                 |

As is clear from the table, 2,6-DMN has a highest melting point of all the DMN isomers. On the other hand, it is known that 2,6-DMN forms a eutectic together with at least one of 1,5-DMN, 2,7-DMN and 2,3-DMN. It is therefore, necessary that the ratio by amount of 2,6-DMN in the isomer mixture to the isomers be more than the compositional ratio of the eutectic in order to precipitate 2,6-DMN as a crystal by means of crystallization from the mixture of the isomers. That is to say, the condition under which 2,6-DMN is at first precipitated as a crystal by cooling is that the molar ratios of 1,5-DMN, 2,7-DMN and 2,3-DMN each in the mixture of the isomers to 2,6-DMN in the same are not more than 1.9, 1.4 and 1.1, respectively.

As a method for isolating 2,6-DMN from the mixture of the isomers, there are proposed a crystallization method, an adsorption method, a method in which 2,6-DMN is caused to form a complex by the use of a certain kind of an organic compound, the resultant complex is separated and then it is decomposed to recover 2,6-DMN, and the like methods. Of these methods, crystallization method is most simple, convenient and suitable as an industrial isolation method.

In particular, in the case of producing a mixture of isomers consisting essentially of 1,5-, 1,6- and 2,6-DMN from o-xylene and butadiene and isolating 2,6-DMN therefrom, a crystallization method is effective because of the comparatively small number of isomers in the starting raw material to be purified. In the case of methylating naphthalenes, isomerizing the reaction product and isolating 2,6-DMN or in the case of isolating the same from a tar fraction or a petroleum fraction, the combination of an adsorption method and a crystallization method is usually employed, since 2,6-DMN needs to be isolated from the mixture of a large number of isomers.

In the case of recovering 2,6-DMN by separating it from a mixture of various DMN isomers typified by the mixture of DMN isomers comprising 1,5-, 1,6- and 2,6-DMN as the principal components which mixture is obtained from o-xylene and butadiene, isomerization is necessary in order to enhance the yield of 2,6-DMN. Specifically it is effective to enhance the yield of 2,6-DMN by repeating the steps of isomerizing the mixture of DMN isomers obtained as the mother liquor separated from precipitated 2,6-DMN to enhance 2,6-DMN concentration; and recovering 2,6-DMN by separating it from the resultant mixture of DMN isomers.

It is well known that in the case of isomerizing DMN, isomerization between adjacent β-positions and isomerization of methyl-migration from one ring to another are unlikely to take place as compared with that between α-position and β-position. Specifically, the above-mentioned 10 DMN isomers are classified into four groups, namely A to D groups as undermentioned with regard to isomerization, and isomerization among different groups is unlikely to take place as compared with that in the same group.

Group A - - - 1,5-DMN, 1,6-DMN, 2,6-DMN
Group B - - - 1,8-DMN, 1,7-DMN, 2,7-DMN
Group C - - - 1,4-DMN, 1,3-DMN, 2,3-DMN
Group D - - - 1,2-DMN There is disclosed in Japanese Patent Publication No. 24331/1982 (U.S. Pat. No. 3,957,896) a process for producing 2,6-DMN by utilizing the fact that the use of a specific isomerization catalyst causes isomerization to a different group which process comprises isomerizing, in the presence of such a catalyst, a mixture of DMN which contains to some extent, DMN not belonging to 2,6-DMN group as a starting raw material, crystallizing the resultant isomerization liquid product, separating 2,6-DMN therefrom and recycling for reuse the mother liquor separated from 2,6-DMN. However, crystallization was carried out according to the above-mentioned process by the present inventors by the use of the mixture of isomers which was obtained through the isomerization of DMN containing to some extent, DMN not belonging to 2,6-DMN group with the result that highly pure 2,6-DMN crystal was proved to be unobtainable.

SUMMARY OF THE INVENTION

It is the general object of the present invention to provide an industrially advantageous process for producing highly pure 2,6-DMN in high recovery rate based on a starting raw material by isolating and recovering 2,6-DMN through the crystallization of a mixture of DMN isomers which is obtained by isomerizing, as a starting raw material, a mixture of DMN comprising 1,5-DMN as a principal component; and a process for producing a 2,6-naphthalenedicarboxylic acid from the 2,6-DMN which is obtained by the above-mentioned process.

Intensive research and investigation were made by the present inventors on the process for producing highly pure 2,6-DMN through crystallization, starting from a mixture of DMN comprising 1,5-DMN as a principal component. As a result, it has been found that highly pure 2,6-DMN is industrially easily obtained by distilling the mother liquor formed in the crystallization step of a mixture of DMN isomers which is produced by isomerizing a mixture of DMN so as to remove the components each having a higher boiling point than DMN and the components each having a lower boiling point than DMN, and recycling the DMN fraction for reuse through an isomerization step; that highly pure 2,6-DMN having purity of 98% or higher can be isolated and recovered at high yield by restricting the concentrations of 2,7-DMN, monomethylnaphthalene (hereinafter abbreviated to "MMN") and trimethylnaphthalene (hereinafter abbreviated to "TMN") that are contained in the starting raw material for crystallization each to a prescribed level; and that a highly pure 2,6-naphthalenedicarboxylic acid is easily obtained by subjecting the 2,6-DMN thus obtained to liquid-phase oxidation. The present invention has been accomplished on the basis of such finding.

Specifically, the present invention provides a process for producing highly pure 2,6-DMN from a mixture of DMN which process comprises (A) the isomerization step of isomerizing a mixture of DMN in the presence of a catalyst, (B) the crystallization step of precipitating 2,6-DMN crystal by means of crystallization in the presence of a solvent from the isomerization reaction product formed in the preceding (A) isomerization step, (C) the crystal isolation step of isolating and recovering the 2,6-DMN crystal precipitated in the preceding (B) crystallization step, and (D) the distillation step of distilling the mother liquor formed after the isolation of the crystal precipitated in the preceding (C) crystal isolation step to obtain DMN fraction by removing the components each having a higher boiling point than DMN and the components each having a lower boiling point than DMN, said steps being carried out in turn, and said DMN fraction being circulated in part or in whole to the preceding isomerization step (A).

The present invention also provides a process for producing a 2,6-naphthalenedicarboxylic acid which comprises subjecting the 2,6-DMN obtained by the above-mentioned process to liquid-phase oxidation.

SYMBOLS

1: isomerization step 2: crystallization step
3: crystal separation step 4: distillation step
A: DMN mixture as starting raw material
B: mother liquor C: DMN fraction
D: low boiling portion E: high boiling portion
F: 2,6-DMN crystal

DESCRIPTION OF PREFERRED EMBODIMENT

Figure 1:
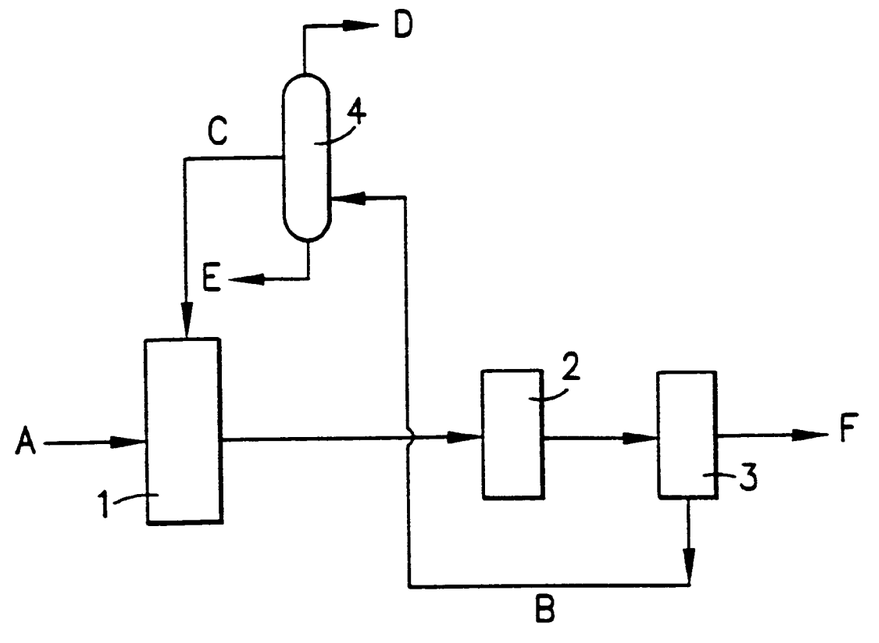
The Figure is a schematic block flow diagram illustrating one example of the steps in the process for producing highly pure 2,6-DMN according to the present invention.

The process for producing 2,6-DMN according to the present invention is composed of four steps including isomerization step, crystallization step, crystal separation step and distillation step. The Figure is a schematic block flow diagram illustrating one example of the production steps.

In the isomerization step 1, a DMN mixture as the starting raw material A comprising 1,5-DMN as a principal component is isomerized in the presence of a catalyst. The resultant isomerization reaction product is sent to the crystallization step 2, where it is subjected to crystallization treatment to precipitate 2,6-DMN crystal. Then it is sent to the crystal separation step 3, where highly pure 2,6-DMN crystal F is recovered by separation. The mother liquor B separated from 2,6-DMN crystal is sent to the distillation step 4, where the high boiling portion E having a boiling point higher than that of the DMN isomer with a highest boiling point among the DMN isomers and the low boiling portion D having a boiling point lower than that of the DMN isomer with a lowest boiling point there among are removed and the DMN fraction C is returned to the isomerization step and circulated through the system.

As the DMN mixture as the starting raw material comprising 1,5-DMN as a principal component, there is preferably used the DMN mixture comprising 1,5-DMN as a principal component which is obtained from o-xylene and butadiene as raw materials.

The DMN mixture introduced in the isomerization step is a DMN mixture comprising 1,5-DMN, 1,6-DMN and 2,6-DMN as principal components, since it is the mixture of the DMN mixture comprising 1,5-DMN as a principal component; and the DMN fraction obtained by distilling the mother liquor separated through the crystallization of 2,6-DMN.

With regard to the process according to the invention, the performance result of the isomerization reaction exerts great influence upon the process as a whole. Specifically, the higher the isomerizational conversion to 2,6-DMN, the higher the economical efficiency of the process, since the yield per pass in the crystal separation step increases with a increase in the isomerizational conversion, thereby decreasing the DMN circulation rate. If the reaction is accompanied by disproportionation and/or isomerization to an isomer belonging to a different group, the resultant crystal is deteriorated in purity. Accordingly, these side reactions need to be suppressed to a minimum. In particular, an isomer belonging to a different group from the group of 2,6-DMN, for example, 2,7-DMN, when formed, is difficult to remove by distillation and is accumulated in the production system during circulation. Such accumulation not only lowers the purity of crystal, but also necessitates the taking out of the DMN fraction in part, whereby the yield of 2,6-DMN is deteriorated.

The isomerization catalyst to be used in the isomerizatiori step is not specifically limited, provided that it shows acidity, but is exemplified by a solid acid, a mineral acid and hydrofluoric acid. Examples of solid acids include silica-alumina, alumina, X-form zeolite, Y-form zeolite, mordenite and β-form zeolite. Of these zeolite is preferable. Suitable zeolite is the zeolite in which cations in part or in whole are replaced with hydrogen or a metal. For the purpose of enhancing isomerizational coversion to 2,6-DMN and suppressing disproportionation as well as isomerization into a different group, it is preferable to adopt the mordenite of hydrogen substituted form, especially the mordenite being substantially of hydrogen form and having a silica/alumina molar ratio of at least 100. The zeolite catalyst is usable even in the form of powder, but a molded catalyst is used depending upon the reaction process. As a molding aid in the case of molding, there is usually used alumina, silica, clay or acid clay, of which alumina and silica are preferable.

The reaction process applicable to the isomerization reaction is not specifically limited, but is exemplified by any of batch-wise system and flow system, of which flow system is preferably from the industrial viewpoint. As the flow system, any of fixed bed, moving bed and fluidized bed is applicable to the system and among them, fixed bed flow system is prevailing. The reaction may be carried out in any of liquid phase and gaseous phase without specific limitation to the pressure in the reaction system.

The DMN as the starting raw material for isomerization may be used as such or after being diluted with a solvent or a gas. The use or nonuse of a diluent such as a solvent is determined taking into consideration overall economical efficiency of all the steps including the isomerization step, crystallization step, crystal separation step and distillation step. Preferable examples of the solvent as a diluent include aliphatic saturated hydrocarbons such as pentane, hexane, heptane, octane, nonane, decane, undecane and dodecane, and alicyclic saturated hydrocarbons such as cyclopentane and cyclohexane. In the case of using a gas as a diluent, there is used a gas which is inactive to the isomerization reaction such as nitrogen, carbon dioxide, hydrogen and argon. It is also possible to carry out the isomerization reaction by the use of same solvent as that to be used in the crystallization step.

The isomerization reaction temperature varies depending upon the catalyst species and the reaction process, and is usually 100 to 500° C., preferably 150 to 300° C. The weight hourly space velocity (WHSV) is usually 0.1 to 10 $hr^{-1}$, preferably 0.2 to 5 $hr^{-1}$. In the case where the reaction temperature is unreasonably high or the WHSV is unreasonably low, side reaction such as isomerization into a different group and disproportionation is apt to take place, whereas an unreasonably low reaction temperature results in reduced isomerizational conversion to 2,6-DMN.

Subsequent to the isomerization step, 2,6-DMN crystal is precipitated in the crystallization step, and the crystal is separated and recovered in the crystal separation step. Usually, no separating operation is required between the isomerization step and the crystallization step. However, in the case of using a solvent in the isomerization step, the operation of separating the solvent is sometimes necessary depending on the kind of the solvent. The crystallization method may be a cooling method, solvent distillation method or the like without specific limitation. The crystallization process may be any of batch-wise process and continuous process.

In the case where an isomerization reaction product obtained by isomerizing DMN under a solventless condition is crystallized as it is, the resulting crystal is poor in filterability, thus making it difficult to improve crystal purity by rinsing. As opposed to the foregoing, crystallization in the presence of a solvent according to the present invention can improve the crystal properties and produce crystal having favorable filterability.

Examples of the solvent to be coexistent with DMN in crystallization include aliphatic saturated hydrocarbons, alicyclic saturated hydrocarbons, aromatic hydrocarbons and alcohols. Of these, there are preferably used aliphatic saturated hydrocarbons exemplified by pentane, hexane, heptane, octane, nonane, decane, undecane and dodecane and alicyclic saturated hydrocarbons exemplified by cyclopentane, methylcyclopentane, cyclohexane, methylcyclohexane and decalin. By the use of any of these solvents, DMN crystal having improved filterability and high purity is obtained in high efficiency. In addition, the solvent which has been used in the isomerization step can be used as such as the solvent for the crystallization step.

For the purpose of preventing the trouble due to the adhesion of crystal in the crystallizer in the crystallization step, the following methods can be used: ① a method in which a crystallizer equipped with a heat transfer surface is used and a coolant is passed in contact with the heat transfer surface, and the difference in temperature between the coolant and the solution containing DMN isomers is maintained at 40° C. or lower; ② a method in which the solution containing DMN is concentrated by depressurizing the crystallizer or treating the solution with an inert gas thereby evaporating the solvent; and ③ a method in which the solution containing DMN isomers is cooled by introducing a liquefied gas into the solution, thereby evaporating the gas.

Moreover, in order to suppress the agglomeration of crystal, the following methods may be used: ① a method in which the average retention time of the crystal in the crystallizer is restricted to 6 hours at the longest; ② a method in which the agglomerate of the crystal is destroyed by circulating the slurry in the crystallizer by means of a circulation pump which is installed outside the crystallizer; and ③ a method in which the content in the crystallizer is stirred to the extent that the agglomeration of the crystal is suppressed.

Furthermore in order to accelerate crystal growth, the following methods may be used: ① a method in which the procedures of heating the slurry in the crystallizer to dissolve a part of the crystal, and recrystallizing the dissolved crystal are carried out at least one time; and a method in which 2,6-DMN crystal which has been separately prepared is added as the seed crystal in the crystallizer.

The slurry which has been subjected to crystallization treatment to precipitate 2,6-DMN crystal is sent to the subsequent crystal separation step, where the precipitated crystal is separated and recovered. The separation recovery equipment in the crystal separation step is not specifically limited, but may be selected for use from the conventionally used equipment for solid-liquid separation such as a centrifugal separator and a filtering apparatus including a filter. It is preferable in particular, that the slurry obtained by crystallization be continuously filtered by the use of a rotary vacuum filter (hereinafter abbreviated to "RVF"). RVF is a continuous solid-liquid separation apparatus in which a part of a cylindrical filter cloth is immersed in a slurry to filter the slurry with suction by rotating the filter cloth. In a RVF, the cake which is formed on the filter cloth by immersing the filter cloth in the slurry and depressurizing the cylinder inside to suck mother liquor, is washed with a suitable rinsing liquid and is peeled off from the filter cloth for recovery thereof. The recovered cake contains a solvent and the rinsing liquid, but can be made into highly pure 2,6-DMN by removing the solvent and the rinsing liquid by means of distillation or the like method.

A RVF is imparted with excellent advantages in that the use thereof enables not only solid-liquid separation but also a series of continuous operations including cake rinsing, suction of the rising liquid and cake peeling off and further enables highly pure 2,6-DMN to be produced by continuous single-stage operation. A RVF is advantageous also in that mechanical troubles are less apt to occur because of a low rotational speed and that the maintenance work is simplified.

In the case of solid-liquid separation by means of a RVF, the steps of immersing a filter cloth in slurry, sucking mother liquor, rinsing cake and peeling the cake are carried out in turn. The mother liquor remaining in the cake is sucked and then the cake collected on the filter cloth which has been immersed in the slurry is washed with a proper rinsing liquid. Preferably, the rinsing liquid is the same as the solvent which is used in the crystallization. Subsequently the rinsing liquid remaining in the cake is sucked, and the cake is peeled off from the filter cloth and recovered. The solvent and rinsing liquid still remaining in the cake are removed from the cake thus recovered to afford highly pure 2,6-DMN.

In this case the filter cloth is preferably washed from the time of the cake peeling to the time of the filter cloth immersion in the slurry. This washing enables 2,6-DMN which is the cause for filter cloth plugging, to be dissolved and the filtering treatment capacity to be steadily maintained for a long period of time without discontinuing the RVF operation. The operation of washing the filter cloth may be carried out continuously at all times or intermittently according to the degree of filter cloth plugging.

The cleaning liquid for the filter cloth to be used therein is to be liquid under the operational conditions, capable of dissolving 2,6-DMN and compatible with the mother liquor and the rinsing liquid and preferably be low in reactivity with 2,6-DMN and easily separable from DMN. The cleaning liquid is not specifically limited, but is preferably the same as the solvent for crystallization or the cake rinsing liquid from the viewpoint of recovery and separation of the mother liquor, the rinsing liquid and the cleaning liquid.

The above-mentioned aliphatic and alicyclic saturated hydrocarbons suitable for crystallization are imparted with all the necessary requirements, that is, being in the form of liquid, capability of dissolving 2,6-DMN, compatibility with the mother liquor and the rinsing liquid, low reactivity with 2,6-DMN and easiness of separation from DMN, and thus are preferably usable as the cleaning liquid for the filter cloth.

The cleaning of the filter cloth is intended for dissolving on the filter cloth, the crystal precipitated by cooling, and is conducted preferably at a temperature not lower than the filtration temperature, that is, the slurry temperature. The use of a hot solvent as the cleaning liquid for the filter cloth enables high performance cleaning effect, thus minimizing the period of time required for the cleaning as well as the amount of the cleaning liquid to be used.

The amount of the cleaning liquid per unit time for achieving satisfactory cleaning effect is determined by the filter cloth area and the filter constitution. In the case of using a hot solvent which enables high performance cleaning effect, the amount of the cleaning liquid to be used can be decreased by intermittently carrying out the cleaning at a prescribed time interval. The aforesaid amount per unit time and cleaning hours are determined so as to select optimum conditions taking the expectable cleaning effect into consideration.

The mother liquor separated from the crystal is sent to the distillation step, where the components each having a higher boiling point than DMN and the components each having a lower boiling point than DMN are removed, and the DMN fraction alone is returned to the isomerization step and circulated through the system. As mentioned hereinbefore, DMN has 10 isomers having a different boiling point from one another. The high boiling portion having a boiling point higher than that of the DMN isomer with a highest boiling point among the DMN isomers and the low boiling portion having a boiling point lower than that of the DMN isomer with a lowest boiling point there among are removed by separation, and the DMN fraction thus obtained is circulated in part or in whole through the system for reuse. Since the solvent for crystallization, which is contained in the mother liquor separated from the crystal, is usually contained in the low boiling portion, it is separated by distillation and is returned for reuse to the isomerization step or the crystallization step.

In order to obtain highly pure 2,6-DMN in the above-mentioned process, it is preferable to restrict 2,7-DMN concentration based on DMN series in the starting raw material for the crystallization step to at most 10% by weight, and it is more preferable to restrict 2,7-DMN, MMN and TMN to concentrations at the highest of 5% by weight, 3% by weight and 10% by weight, respectively.

Accordingly, it is necessary to control the amounts of MMN and TMN in the DMN fraction to be circulated through the system taking into consideration the amounts of MMN and TMN in the DMN to be freshly fed in the isomerization step as well as the by production amounts of MMN and TMN, when by-produced in said step.

In the case where the isomer of a different group such as 2,7-DMN is contained in the DMN to be freshly fed in the isomerization step, and in the case where such isomer of a different group such as 2,7-DMN is formed in the step, it is difficult to separate such isomer of different group by means of distillation. It is therefore, required to take out part of DMN along with the high boiling and low boiling components before, during or after the distillation step, preferably during the distillation for the purpose of controlling 2,7-DMN concentration in the starting raw material for crystallization.

The amount of the DMN to be taken out for controlling 2,7-DMN concentration therein is determined, taking into account the economical efficiency of the production process as a whole including the amounts of the isomers of different groups in the DMN to be freshly fed, the amounts of such isomers produced in the isomerization step, the purity of the crystal obtainable in the crystallization step and the amount of DMN to be circulated. In addition, since a slight amount of 2,7-DMN inherently accompanies the crystal, it is made possible to prevent 2,7-DMN from being accumulated in the system by discharging the slight amount of 2,7-DMN accompanying the crystal as such outside the system, provided that the amount of the isomers of different group in the DMN to be freshly fed and the amount of such isomer formed in the isomerization step are each not more than a definite value.

The mixture of DMN comprising as a principal component, 1,5-DMN which is produced from o-xylene and butadiene belongs to the foregoing 2,6-group, and is isomerized into an isomerization reaction product composed mainly of 1,5-, 1,6-and 2,6-DMNs. The mother liquor separated from the 2,6-DMN crystal which is formed from the aforesaid isomerization reaction product contains 1,5-DMN and 1,6-DMN as principal components, and can be circulated for use as a starting raw material for isomerization. In the case of isomerization reaction, however, side reactions are prone to occur which are exemplified by the formation of MMN and TMN due to disproportionation and the formation of isomers belonging to 2,7-group due to isomerization into a different group. Of these, MMN and TMN can be removed by distillation. However, the isomers of a different group are difficult to remove by distillation, and are accumulated in the production system, when the mother liquor separated from the precipitated 2,6-DMN crystal is circulated through the reaction system.

It is well known that, in the case of separating 2,6-DMN from the mixture of DMN isomers by means of crystallization, 2,6-DMN forms a eutectic together with at least one of 2,7-DMN, 1,5-DMN and 2,3-DMN. The compositional ratio in the eutectic of 2,6-DMN to each of the three other isomers is as follows.

2,6-DMN/2,7-DMN=1.4
2,6-DMN/1,5-DMN=1.9
2,6-DMN/2,3-DMN=1.1

It follows, therefore in principle from the eutectic theory, that when an isomerization reaction product of DMN containing 2,6-DMN having a compositional ratio exceeding the above-listed figure is cooled, 2,6-DMN is precipitated as crystal; and besides, the components other that 2,6-DMN are attached as the mother liquor onto the crystal thus precipitated and can be removed by rinsing the crystal with a solvent such as n-heptane.

Nevertheless as a result of investigation made by the present inventors on the method for recovering 2,6-DMN by separating it through crystallization from the isomerization reaction product of DMN, it has been found that 2,7-DMN, 2-MMN and part of TMN isomers each behave differently from the other isomers as impurities.

Detailed investigation was made by the present inventors on the relation between the concentration of the impurities in the raw material for crystallization and the concentration of impurities remaining in the objective crystal. As a result, there was observed a phenomenon that in the case where 2,7-DMN, MMN and/or TMN are present to a certain or more extent in the raw material for crystallization, 2,7-DMN, 2-MMN and/or part TMN of isomers remain in the objective crystal in amounts larger than the amount derived from eutetic theory, thereby making it difficult to obtain highly pure crystal.

As a result of further investigation, it has been found that the components such as 1,5-/1,6-DMNs, 1-MMN and the isomer other than the above-remaining isomer in TMN that are contained in DMN isomerization reaction product to be used for raw material for crystallization can easily be removed by rinsing 2,6-crystal after precipitation, and the concentration of such impurities steadily decreases with an increase in the amount of a rising liquid, but that 2,7-DMN, 2-MMN and part of TMN isomers hardly change in concentration even after rinsing the crystal and they are inevitably drawn and incorporated inside the crystal at the time of precipitation of 2,6-DMN as crystal instead of being attached, as the components of the mother liquor, onto the surface of the crystal.

The amounts of 2,7-DMN, 2-MMN and part of TMN isomers that are inevitably contained in the crystal at the time when the 2,6-DMN crsytal is precipitated are determined approximately by the ratio by amount of each component to the dimethylnaphthalene series in the raw material for crystallization. When 10 parts by weight of 2,7-DMN is contained in 100 parts by weight of dimethylnaphthalene series, the amount of 2,7-DMN contained in 2,6-DMN crystal accompanied therewith is about 0.7 to 1.4% by weight. When 5 parts by weight of 2,7-DMN is contained in 100 parts by weight of dimethylnaphthalene series, the amount of 2,7-DMN contained in 2,6-DMN crystal accompanied therewith is about 0.4 to 0.8% by weight. On the other hand, when 5 parts by weight of MMN or TMN is contained in 100 parts by weight of dimethylnaphthalene series, the amount of 2-MMN or part of TMN isomers contained in 2,6-DMN crystal accompanied therewith is about 0.7 to 1.3% by weight or about 0.2 to 0.6% by weight, respectively.

It is therefore desirable, in order to obtain 2,6-DMN having high purity of 98% or higher, that the concentration of 2,7-DMN based on dimethylnaphthalene series in the raw material for crystallization be set on at most 10% by weight when the raw material is almost free from MMN and TMN.

In the case where a considerable amount of MMN or TMN is contained in the raw material for crystallization, it is desirable, in order to restrict the concentrations of 2,7-DMN, MMN and TMN remaining in 2,6-DMN crystal to at most 0.5% by weight, respectively, that the concentrations of 2,7-DMN, MMN and TMN based on dimethylnaphthalene series in the raw material for crystallization be set on at most 5%, 3% and 10% by weight, respectively.

Specifically, although it is said that judging from the above-listed compositional ratio, 2,6-DMN crystal alone is precipitated by cooling the raw material for crystallization having a 2,7-DMN/2,6-DMN molar ratio of less than 1.4, it has been clarified by the present invention that a slight amount of 2,7-DMN remaining in the 2,6-DMN crystal is not reduced in its amount even if crystal rinsing is carried out. Thus, it is made important to restrict the concentration of 2,7-DMN in the starting raw material for crystallization to the above-mentioned percentage by weight.

MMN has two isomers including 1-MMN and 2-MMN according to the position of a methyl group. Of these, 2-MMN remains inside the crystal, while 1-MMN as a component of the mother liquid is attached onto the crystal and can easily be removed by rinsing. TMN has 16 isomers according to the positions of three methyl groups. It is not clear at the present time which of the isomers remain inside the crystal, but part of the isomers having a methyl group at β-position presumably remains inside the crystal. TMN remaining thereinside is only part of the 16 isomers, and any other isomer as a component of the mother liquor is attached onto the crystal as is the case with 1-MMN, and thus can easily be removed by rinsing.

In the case of isomerizing DMN as the starting raw material, MMN and TMN that are contained in DMN are simultaneously isomerized into a mixture of MMN isomers and a mixture of TMN isomers in the resultant isomerization reaction product. The amount of MMN in the isomerization reaction product varies depending upon the amount of MMN in the starting raw material for isomerization and the extent of disproportionation which accompanies the isomerization. The ratio by amount of 2-MMN to 1-MMN in MMN in whole varies depending on the catalyst species used in isomerization and reaction conditions, and is in the range of from 1 to 3, approximately. The kind and amount of TMN isomers in the isomerization reaction product varies depending upon the kind and amount of TMN isomers in the starting raw material for isomerization as well as the extent of disproportionation which accompanies the isomerization. The ratio by amount of the TMN isomers remaining inside the crystal to the TMN isomers easily removable as the components of the mother liquor varies to some extent depending upon the catalyst species used in the isomerization and reaction conditions, and is presumably within a definite range as is the case with MMN.

The present invention also provides a process for producing a 2,6-naphthalenedicarboxylic acid by subjecting 2,6-DMN thus obtained to liquid-phase oxidation.

It is preferable in the above-mentioned process that the 2,6-DMN be produced by subjecting a mixture of DMN comprising as a principal component, 1–5 DMN obtained from o-xylene and butadiene as raw materials to the liquid-phase oxidation comprising the above-mentioned steps of (A), (B), (C) and (D).

The liquid-phase oxidation process for 2,6-DMN can be selected for use from the conventional well-known processes without specific limitation. In general, mention may be made of a process in which 2,6-DMN is subjected to liquid-phase oxidation by molecular oxygen in a solvent such as acetic acid in the presence of a catalyst of Co-Mn-Br system, and more specifically, of a process in which 2,6-DMN is subjected to liquid-phase oxidation by air in a solvent comprising acetic acid or water-containing acetic acid containing a small amount of water in the presence of a catalyst composed of a cobalt compound, a manganese compound and a bromine compound under reactional conditions including a pressure of 5 to 40 kg/cm$^2$G, approximately and a temperature of 180 to 250° C., approximately, which process enables the production of 2,6-naphthalenedicarboxylic acid at a high yield of 80% or more. The catalyst is used in amounts of usually 0.002 to 0.1 mol as cobalt atom, 0.01 to 0.2 mol as manganese atom and 0.01 to 0.2 mol as bromine atom each based on one mol of 2,6-DMN as the starting raw material. 2,6-naphthalenedicarboxylic acid thus formed is taken out from the reaction liquid product by a conventional method. The oxidation process may be any of batch-wise system and continuous system.

According to the process of the present invention for producing 2,6-DMN, highly pure 2,6-DMN useful as a raw material for 2,6-naphthalenedicarboxylic acid is efficiently obtained in high yield in an industrially advantageous manner preferably by using a mixture of DMN comprising as a principal component, 1,5-DMN obtained from o-xylene and butadiene as raw materials.

By subjecting the 2,6-DMN thus obtained to liquid-phase oxidation, a highly pure 2,6-naphthalenedicarboxylic acid is industrially advantageously produced which is useful as a starting raw material for high performance polyester, and the like.

In the following, the present invention will be described in more detail with reference to working examples, which however shall not limit the present invention thereto. The concentration of each of the components in the following working examples, comparative examples and reference example was obtained by gas chromatography. The abbreviations used in the working examples, comparative examples and reference example are detailed as follows.

DMN dimethylnaphthalene

MMN monomethylnaphthalene

TMN trimethylnaphthalene

L.B. low boiling components having a lower boiling point than DMN, excluding MMN H.B high boiling components having a higher boiling point than DMN, excluding TMN WHSV weight hourly space velocity (g. of raw material/g. of catalyst. hr)

EXAMPLE 1

A mixture of DMN isomers comprising, as a principal component, 1,5-DMN which had been synthesized from o-xylene and butadiene was isomerized in the presence of mordenite type H as the catalyst (produced by Tosoh Corporation) to afford a DMN isomerization reaction product. 200 g of the DMN isomerization reaction product thus produced and 100 g of n-heptane were placed in a 400 milliliter (mL) glass container equipped with a stirrer under stirring and heating to 80° C. to dissolve the reaction product. Thereafter the resultant solution was gradually cooled under stirring to 20° C. to precipitate crystal. The content in the glass container was filtered by suction with a G2 glass filter (standard maximum diameter of opening of 100 to 150 μm), and the crystal thus obtained was rinsed three times with 20 g of n-heptane at 20° C. The chemical compositions of the DMN isomerization product as the starting raw material for crystallization, of the crystal after filtration and of the crystal after rinsing are given in Table 1. Such impurities as 1,5-DMN, 1-6-DMN, L.B. and H.B. were each steadily removed after every rinsing, with the result that highly pure 2,6-DMN crystal was obtained in an amount of 57.4 g.

TABLE 1

| | Composition (wt %) | | | | | | | | | |
|---|---|---|---|---|---|---|---|---|---|---|
| | DMN | | | | | | | | | |
| | 2,6- | 1,6- | 1,5- | 2,7- | others | MMN | TMN | L. B | H. B | Total |
| Starting raw material | 40.29 | 42.21 | 14.88 | 0.20 | 0.10 | 0.22 | 0.10 | 1.20 | 0.80 | 100.00 |
| After filtration | 92.15 | 5.91 | 1.58 | 0.03 | 0.00 | 0.04 | 0.01 | 0.18 | 0.10 | 100.00 |
| After 1st rinsing | 96.95 | 2.33 | 0.61 | 0.02 | 0.00 | 0.04 | 0.00 | 0.02 | 0.03 | 100.00 |
| After 2nd rinsing | 98.74 | 0.97 | 0.23 | 0.02 | 0.00 | 0.04 | 0.00 | 0.00 | 0.00 | 100.00 |
| After 3rd rinsing | 99.19 | 0.60 | 0.15 | 0.02 | 0.00 | 0.04 | 0.00 | 0.00 | 0.00 | 100.00 |

In addition, the above-mentioned mixture of DMN isomers comprising -,5-DMN as a principal component was incorporated with 2,7-DMN, MMN and TMN and was subjected to isomerization, crystallization, filtration and rinsing in the same manner as the foregoing. The chemical compositions of the DMN isomerization reaction product as the starting raw material for crystallization, of the crystal after filtration and of the crystal after rinsing are given in Table 2. It is understood that such impurities as 1,6-DMN, 1,5-DMN, other DMN, L.B. and H.B are steadily romoved by rinsing, whereas 2,7-DMN, MMN and TMN are difficult to remove by rinsing.

resultant crystal based on the amount thereof in the starting raw material for crystallization.

Thereafter, the mother liquor separated from the crystal along with the rinsing liquid were distilled to afford DMN fraction (1), the amount of which was 95% by weight of the DMN contained in the mother liquor and the rising liquid. The concentration of 2,7-DMN in the DMN fraction (1) was 2.94% by weight. The ratio by weight of the total sum of the DMN taken out as DMN crystal and the DMN which could not be recovered at the time of distillation to the DMN fraction (1) was 31:69.
(Cycle 2)

TABLE 2

| | Composition (wt %) | | | | | | | | | |
|---|---|---|---|---|---|---|---|---|---|---|
| | DMN | | | | | | | | | |
| | 2,6- | 1,6- | 1,5- | 2,7- | others | MMN | TMN | L. B | H. B | Total |
| Starting raw material | 30.03 | 32.45 | 10.89 | 6.87 | 2.91 | 3.56 | 11.28 | 1.15 | 0.86 | 100.00 |
| After filtration | 91.81 | 4.10 | 1.01 | 0.87 | 0.15 | 0.86 | 0.97 | 0.12 | 0.11 | 100.00 |
| After 1st rinsing | 95.71 | 1.81 | 0.43 | 0.61 | 0.06 | 0.63 | 0.69 | 0.04 | 0.02 | 100.00 |
| After 2nd rinsing | 97.34 | 0.72 | 0.17 | 0.53 | 0.01 | 0.56 | 0.66 | 0.01 | 0.00 | 100.00 |
| After 3rd rinsing | 97.99 | 0.22 | 0.09 | 0.52 | 0.00 | 0.55 | 0.63 | 0.00 | 0.00 | 100.00 |

EXAMPLE 2

(Cycle 1)

A mixture of DMN isomers containing 2% by weight of 2,7-DMN, etc. as shown in Table 3 as the starting raw material was isomerized under liquid-phase flow system and atmospheric pressure at a reaction temperature of 220° C. at a WHSV of 1.0 hr$^{-1}$ in the presence of a catalyst (alumina content of 20% by weight) prepared by molding with alumina, mordenite type H (silica/alumina molar ratio of 203, produced by Tosoh Corporation). The resultant isoiverization reaction product shown in Table 3 as reaction product (1) was incorporated with the same amount of n-heptane, heated to 80° C. to dissolve the reaction product and then cooled to 20° C. to precipitate crystal. The slurry containing the crystal was filtered by suction with a G2 glass filter, and the crystal thus obtained was rinsed with n-heptane cooled to 20° C. in an amount by weight half the reaction product. As a result, there was obtained 2,6-DMN crystal having the chemical composition given in Table 3 as "Crystal (1)" in a recovery rate of 64.2%. Here, the recovery rate is the percentage of the amount of 2,6-DMN in the resultant crystal based on the amount thereof in the starting raw material for crystallization.

DMN as the starting raw material and the DMN fraction (1) were blended at a ratio by weight of 31:69, and the resulting blend was isomerized under the same conditions as in Cycle (1) to afford the reaction product (2) having the chemical composition as given in Table 3. The resultant reaction product (2) was subjected to crystallization, filtration and rinsing under the same conditions as in Cycle (1) to afford DMN crystal having the chemical composition shown in Table (3) as crystal (2) at a recovery rate of 64.1%.

Further, the mother liquor separated from the crystal along with the rinsing liquid were distilled in the same manner as in Cycle (1) to afford DMN fraction (2), the amount of which was 95% by weight of the DMN contained in the mother liquor and the rinsing liquid. The concentration of 2,7-DMN in the DMN fraction (2) was 3.18% by weight. The ratio by weight of the total sum of the DMN taken out as DMN crystal and the DMN which could not be recovered at the time of distillation to the DMN fraction (2) was 31:69.
(Cycle 3)

DMN as the starting raw material and the DMN fraction (2) were blended at a ratio by weight of 31:69, and the resulting blend was isomerized under the same conditions as in Cycle (1) to afford the reaction product (3) having the chemical composition as given in Table 3. The resultant reaction product (3) was subjected to crystallization, filtration and rinsing under the same conditions as in Cycle (1) to afford DMN crystal having the chemical composition shown in Table (3) as crystal (3) at a recovery rate of 64.1%.

Further, the mother liquor separated from the crystal along with the rinsing liquid were distilled in the same manner as in Cycle (1) to afford DMN fraction (3), the amount of which was 95% by weight of the DMN contained in the mother liquor and the rinsing liquid. The concentration of 2,7-DMN is the DMN fraction (2) was 3.4% by weight. The ratio by weight of the total sum of the DMN taken out as DMN crystal and the DMN which could not be recovered at the time of distillation to the DMN fraction (2) was 31:69.

(Cycles 4 to 5)

In the same manner as above, DMN as the starting raw material and the DMN fraction thus collected were blended, and the resultant blend was subjected to isomerization, crystallization and distillation, repeatedly. The compositions of the reaction products (4), (5) and the crystal (4), (5) that were obtained by the repeated cycles are given in Table 3. As is seen from Table 3, highly pure 2,6-DMN crystal was obtained even after the repeated procedure with minimized accumulation of 2,7-DMN in the mother liquor, since only a small amount of 2,7-DMN was formed in the isomerization reaction.

Further, the mother liquor separated from the crystal along with the rinsing liquid were distilled in the same manner as in Example (2) to afford DMN fraction (1), the amount of which was 95% by weight of the DMN contained in the mother liquor and the rinsing liquid. The concentration of 2,7-DMN in the DMN fraction (1) was 4.22% by weight. The ratio by weight of the total sum of the DMN taken out as DMN crystal and the DMN which could not be recovered at the time of distillation to the DMN fraction (2) was 26:74.

(Cycle 2)

DMN as the starting raw material and the DMN fraction (1) were blended at a ratio by weight of 26:74, and the resulting blend was isomerized under the same conditions as in Cycle (1) to afford the reaction product (2) having the chemical composition as given in Table 4. The resultant reaction product (2) was subjected to crystallization, filtration and rinsing under the same conditions as in Cycle (1) to afford DMN crystal having the chemical composition shown in Table 4 as crystal (2) at a recovery rate of 59.9%.

Further, the mother liquor separated from the crystal along with the rinsing liquid were distilled in the same manner as in Cycle (1) to afford DMN fraction (2), the amount of which was 95% by weight of the DMN contained in the mother liquor and the rinsing liquid. The ratio by weight of the total sum of the DMN taken out as DMN crystal and the DMN which could not be recovered at the time of distillation to the DMN fraction (2) was 26:74.

TABLE 3

| | Composition (wt %) | | | | | | | | | |
|---|---|---|---|---|---|---|---|---|---|---|
| | DMN | | | | | | | | | |
| | 2,6- | 1,6- | 1,5- | 2,7- | others | MMN | TMN | L. B | H. B | Total |
| Starting raw material | 6.9 | 67.3 | 19.1 | 2.0 | 1.7 | 0.5 | 0.7 | 1.2 | 0.6 | 100.00 |
| Reaction product (1) | 42.8 | 40.9 | 9.7 | 2.1 | 1.5 | 0.5 | 0.7 | 1.3 | 0.5 | 100.00 |
| Reaction product (2) | 43.4 | 41.1 | 10.5 | 2.2 | 1.5 | 0.3 | 0.3 | 0.4 | 0.3 | 100.00 |
| Reaction product (3) | 43.3 | 41.0 | 10.6 | 2.4 | 1.6 | 0.2 | 0.3 | 0.3 | 0.3 | 100.00 |
| Reaction product (4) | 43.2 | 41.1 | 10.1 | 2.6 | 1.7 | 0.3 | 0.4 | 0.3 | 0.3 | 100.00 |
| Reaction product (5) | 43.0 | 41.0 | 10.3 | 2.7 | 1.7 | 0.3 | 0.3 | 0.4 | 0.3 | 100.00 |
| Crystal (1) | 99.6 | 0.2 | 0.0 | 0.2 | 0.0 | 0.0 | 0.0 | 0.0 | 0.0 | 100.00 |
| Crystal (2) | 99.6 | 0.2 | 0.0 | 0.2 | 0.0 | 0.0 | 0.0 | 0.0 | 0.0 | 100.00 |
| Crystal (3) | 99.5 | 0.3 | 0.0 | 0.2 | 0.0 | 0.0 | 0.0 | 0.0 | 0.0 | 100.00 |
| Crystal (4) | 99.4 | 0.3 | 0.0 | 0.3 | 0.0 | 0.0 | 0.0 | 0.0 | 0.0 | 100.00 |
| Crystal (5) | 99.4 | 0.3 | 0.0 | 0.3 | 0.0 | 0.0 | 0.0 | 0.0 | 0.0 | 100.00 |

EXAMPLE 3

(Cycle 1)

The procedure in Example 2 was repeated to carry out isomerization except that there was used a catalyst prepared by molding zeolite type USY (silica/alumina molar ratio of 6.1, produced by Tosoh Corporation) with alumina, (alumina content of 20% by weight) in place of mordenite type H (silica/alumina molar ratio of 203) molded with alumina. There was obtained the reaction product (1) as given in Table 4. In the same manner as in Example (2), the reaction product (1) was subjected to crystallization, filtration and rinsing under the same conditions as in Example (2) to afford DMN crystal having the chemical composition shown in Table 4 as crystal (1) at a recovery rate of 60.4%.

(Cycles 3)

In the same manner Example 2, DMN as the starting raw material and the DMN fraction thus collected were blended, and the resultant blend was subjected to isomerization, crystallization and distillation, repeatedly. The compositions of the reaction product (3) and the crystal (3) that were obtained by the repeated cycles are given in Table 4. As is seen from Table 4, the purity of the DMN crystal tends to decrease with repeated procedure, with increasing accumulation of 2,7-DMN in the reaction system, since the amount of 2,7-DMN formed in the isomerization reaction was larger than that in Example 2.

TABLE 4

| | Composition (wt %) | | | | | | | | | |
|---|---|---|---|---|---|---|---|---|---|---|
| | DMN | | | | | | | | | |
| | 2,6- | 1,6- | 1,5- | 2,7- | others | MMN | TMN | L. B | H. B | Total |
| Starting raw material | 6.9 | 67.3 | 19.1 | 2.0 | 1.7 | 0.5 | 0.7 | 1.2 | 0.6 | 100.00 |
| Reaction product (1) | 36.8 | 38.2 | 10.2 | 3.3 | 2.0 | 2.8 | 2.0 | 2.7 | 2.0 | 100.00 |
| Reaction product (2) | 36.5 | 37.8 | 10.0 | 4.6 | 2.4 | 2.6 | 1.9 | 2.8 | 1.4 | 100.00 |
| Reaction product (3) | 36.1 | 36.0 | 10.5 | 5.8 | 2.7 | 2.8 | 1.8 | 2.6 | 1.7 | 100.00 |
| Crystal (1) | 99.1 | 0.2 | 0.0 | 0.2 | 0.0 | 0.3 | 0.2 | 0.0 | 0.0 | 100.00 |
| Crystal (2) | 99.0 | 0.2 | 0.0 | 0.3 | 0.0 | 0.3 | 0.2 | 0.0 | 0.0 | 100.00 |
| Crystal (3) | 98.4 | 0.3 | 0.0 | 0.6 | 0.1 | 0.4 | 0.2 | 0.0 | 0.0 | 100.00 |

EXAMPLE 4

The procedure in Cycle (1) of Example 2 was repeated to carry out isomerization reaction. Then, the procedure in Example 2 was repeated by the use of the resultant reaction product to carry out crystallization, filtration and rinsing except that toluene was used as the solvent in place of n-heptane. As a result DMN crystal having purity of 98.8% was obtained at a recovery rate of 57.2%. The composition of the resultant crystal is given in Table 5. As can be seen from the Table 5, the recovery rate and purity of the crystal were somewhat inferior to the case where n-heptane was used as the solvent.

COMPARATIVE EXAMPLE 1

The procedure in Cycle (1) of Example 2 was repeated to carry out isomerization reaction. Then, the procedure in Example 2 was repeated by the use of 100 g of the resultant reaction product to carry out crystallization and filtration except that the use of n-heptane as the solvent was omitted. After the filtration, the resultant cake was rinsed with 200 g of n-heptane. As a result DMN crystal having purity of 97.8% was obtained at a recovery rate of 64.8%. The composition of the resultant crystal is given in Table 5. The filterability and purity of the crystal were inferior to the case where n-heptane was used as the solvent.

EXAMPLE 5

The procedure in Example 2 was repeated to carry out isomerization, crystallization and distillation, repeatedly except that there was used, as the starting material for isomerization, 1,5-DMN which had been produced from o-xylene and butadiene as raw materials and which had the chemical composition as given in Table 6. The variations in the chemical compositions of the reaction product and the crystal with the repeated cycle are given in Table 6.

It can be seen that highly pure 2,6-DMN crystal was obtained even after the repeated procedure with minimized accumulation of 2,7-DMN in the mother liquor, since only a small amount of 2,7-DMN was contained in the raw material and formed in the isomerization reaction.

TABLE 5

| | Composition (wt %) | | | | | | | | | |
|---|---|---|---|---|---|---|---|---|---|---|
| | DMN | | | | | | | | | |
| | 2,6- | 1,6- | 1,5- | 2,7- | others | MMN | TMN | L. B | H. B | Total |
| Example 4 | 98.7 | 0.5 | 0.2 | 0.3 | 0.0 | 0.1 | 0.1 | 0.0 | 0.1 | 100.00 |
| Comparative Example 1 | 97.6 | 0.8 | 0.3 | 0.5 | 0.1 | 0.2 | 0.2 | 0.1 | 0.2 | 100.00 |

TABLE 6

| | Composition (wt %) | | | | | | | | | |
|---|---|---|---|---|---|---|---|---|---|---|
| | DMN | | | | | | | | | |
| | 2,6- | 1,6- | 1,5- | 2,7- | others | MMN | TMN | L. B | H. B | Total |
| Starting raw material | 0.0 | 0.1 | 99.6 | 0.0 | 0.2 | 0.0 | 0.0 | 0.1 | 0.0 | 100.00 |
| Reaction product (1) | 43.3 | 41.9 | 13.7 | 0.2 | 0.2 | 0.1 | 0.2 | 0.2 | 0.2 | 100.00 |
| Reaction product (2) | 43.5 | 41.9 | 13.7 | 0.3 | 0.2 | 0.1 | 0.1 | 0.1 | 0.1 | 100.00 |
| Reaction product (3) | 43.2 | 41.9 | 13.9 | 0.4 | 0.2 | 0.1 | 0.1 | 0.1 | 0.1 | 100.00 |
| Reaction product (4) | 43.6 | 41.6 | 13.8 | 0.4 | 0.2 | 0.1 | 0.1 | 0.1 | 0.1 | 100.00 |
| Reaction product (5) | 43.2 | 41.9 | 13.7 | 0.5 | 0.3 | 0.1 | 0.1 | 0.1 | 0.1 | 100.00 |
| Crystal (1) | 99.8 | 0.2 | 0.0 | 0.0 | 0.0 | 0.0 | 0.0 | 0.0 | 0.0 | 100.00 |
| Crystal (2) | 99.8 | 0.2 | 0.0 | 0.0 | 0.0 | 0.0 | 0.0 | 0.0 | 0.0 | 100.00 |
| Crystal (3) | 99.7 | 0.3 | 0.0 | 0.0 | 0.0 | 0.0 | 0.0 | 0.0 | 0.0 | 100.00 |
| Crystal (4) | 99.8 | 0.2 | 0.0 | 0.0 | 0.0 | 0.0 | 0.0 | 0.0 | 0.0 | 100.00 |
| Crystal (5) | 99.8 | 0.2 | 0.0 | 0.0 | 0.0 | 0.0 | 0.0 | 0.0 | 0.0 | 100.00 |

REFERENCE EXAMPLE

Starting raw materials for crystallization in 5 numbers containing 2,7-DMN in amounts of about 3%, 6%, 10%, 16% and 20%, respectively each by weight by adding 2,7-DMN to an isomerization reaction product having the chemical composition as given in Table 7. 100 g of each of the starting raw materials, to which was added 100 g of n-heptane, was placed in a 400 mL glass container equipped with a stirrer under stirring and heating to 80° C. to dissolve the reaction product. Thereafter the resultant solution was gradually cooled under stirring to 20° C. to precipitate crystal. The content in the glass container was filtered by suction with G2 glass filter (standard maximum diameter of opening of 100 to 150 μm), and the crystal thus obtained was rinsed three times with 10 g of n-heptane at 20° C. The chemical compositions of the starting raw material for crystallization and of the crystal after the rinsing are given in Table 7.

In the case of a high concentration of 2,7-DMN in the starting raw material for crystallization, 2,7-DMN remaining in the resultant crystal is not removed even by three times of rinsing, thereby making it impossible to obtain highly pure 2,6-DMN crystal. the recovery rates of 2,6-DMN from the starting raw materials of crystallization containing 2,7-DMN in amounts of about 3%, 6%, 10%, 16% and 20%, respectively each by weight were 64.9%, 63.7%, 62.7%, 61.4% and 58.6%, respectively. Thus, the recovery rate of 2,6-DMN decreases with an increase in the concentration of 2,7-DMN in the starting raw material for crystallization.

TABLE 7

| | Composition (wt %) | | | | | | | | | |
|---|---|---|---|---|---|---|---|---|---|---|
| | DMN | | | | | | | | | |
| | 2,6- | 1,6- | 1,5- | 2,7- | others | MMN | TMN | L. B | H. B | Total |
| Isomerization reaction product | 40.29 | 42.21 | 14.88 | 0.20 | 0.10 | 0.22 | 0.10 | 1.20 | 0.80 | 100.00 |
| S.R.M.C.C. 3 wt % | 39.07 | 40.93 | 14.43 | 3.22 | 0.10 | 0.21 | 0.10 | 1.16 | 0.78 | 100.00 |
| 2,7-DMN Crystal | 99.24 | 0.29 | 0.10 | 0.31 | 0.00 | 0.04 | 0.00 | 0.01 | 0.01 | |
| S.R.M.C.C. 6 wt % | 38.02 | 39.83 | 14.04 | 5.82 | 0.09 | 0.21 | 0.09 | 1.15 | 0.75 | 100.00 |
| 2,7-DMN Crystal | 98.93 | 0.29 | 0.09 | 0.64 | 0.00 | 0.04 | 0.00 | 0.01 | 0.00 | |
| S.R.M.C.C. 10 wt % | 36.37 | 38.10 | 13.43 | 9.91 | 0.09 | 0.20 | 0.09 | 1.08 | 0.72 | 100.00 |
| 2,7-DMN Crystal | 98.55 | 0.30 | 0.09 | 1.01 | 0.00 | 0.04 | 0.00 | 0.01 | 0.00 | |
| S.R.M.C.C. 16 wt % | 33.95 | 95.58 | 12.54 | 15.89 | 0.08 | 0.19 | 0.08 | 1.01 | 0.67 | 100.00 |
| 2,7-DMN Crystal | 97.91 | 0.31 | 0.11 | 1.62 | 0.00 | 0.04 | 0.00 | 0.01 | 0.00 | |

TABLE 7-continued

| | Composition (wt %) | | | | | | | | | |
|---|---|---|---|---|---|---|---|---|---|---|
| | DMN | | | | | | | | | |
| | 2,6- | 1,6- | 1,5- | 2,7- | others | MMN | TMN | L. B | H. B | Total |
| S.R.M.C.C. 20 wt % | 32.35 | 33.89 | 11.95 | 19.87 | 0.08 | 0.18 | 0.08 | 0.96 | 0.64 | 100.00 |
| 2,7-DMN Crystal | 97.49 | 0.32 | 0.10 | 2.03 | 0.01 | 0.04 | 0.00 | 0.01 | 0.00 | |

Remarks S.R.M.C.C. = Starting raw material for crystallization containing

EXAMPLE 6

Acetic acid in an amount of 288.9 g was mixed with 3.2 g water, 0.63 g of cobalt acetate quadrihydrate, 5.37 g of manganese acetate quadrihydrate, and 1.92 g of hydrogen bromide (47% aqueous solution) to prepare a catalyst solution. Then, 120.0 g of the above-prepared catalyst solution was fed in a 0.5 liter titanium-made autoclave (reactor) equipped with a stirrer, a reflux condenser and a raw material transfer pump. The balance 180.0 g of the catalyst solution was mixed with 30.0 g of the 2,6-dimethylnaphthalene (DMN) as obtained in Example 1. The resultant mixture was fed in a raw material feed tank and was heated to dissolve 2,6-DMN and prepare a raw material solution. The reaction system was pressurized with nitrogen gas to a regulated pressure of 18 kg/cm$^2$G, and the content in the reactor was heated to 200° C. under stirring. When the temperature and the pressure in the reactor were stabilized, the raw material solution and compressed air were fed in the reactor to start oxidation reaction. The raw material solution was continuously fed in the reactor over a period of one hour, while the flow rate of the feed air was regulated so that the concentration of oxygen in the exhaust gas was made to be 2% by volume. During the above period, the partial pressure of oxygen in the reactor was 0.12 kg/cm$^2$ (absolute pressure). After the feed of the raw material solution was finished, air was continuously fed for 9 minutes.

After the completion of the oxidation reaction, the reactor was cooled to room temperature, and the resultant reaction product was taken out from the reactor and filtered by suction with a glass filter to separate the filter cake in the form of crystal. Thereafter the cake thus separated was cleaned by rinsing with 80.0 g of acetic acid containing 20% by weight of water. The cake was weighed and subsequently dried with a dryer to afford 40.65 g of crude naphthalene-dicarboxylic acid (NDCA) in the form of crystal. Thus the NDCA in the dried crystal was obtained in a purity of 96.5% by weight at a yield of 94.5 mol% based on the 2,6-DMN fed in the reaction system.

What is claimed is:

1. A multi-cyclic process for producing highly pure 2,6-dimethylnaphthalene from a mixture of dimethylnaphthalene wherein each cycle comprises sequentially:
    (A) isomerizing a mixture of dimethylnaphthalene in the presence of a catalyst selected from the group consisting of a catalyst consisting essentially of a mordenite being substantially of a hydrogen form and having a molar ratio of silica to alumina of at least 100 and a catalyst consisting essentially of a mordenite being substantially of a hydrogen form and having a molar ratio of silica to alumina of at least 100 with at least one molding aid selected from the group consisting of alumina and silica, to form an isomerization reaction product,
    (B) crystallizing 2,6-dimethylnaphthalene from the isomerization reaction product, containing at most 10% by weight of 2,7-dimethylnaphthalene based on the total amount of dimethylnaphthalene compounds contained in the isomerization reaction product formed in step (A) in the presence of at least one solvent selected from the group consisting of hexane, heptane, octane, isooctane, nonane, methylcyclopentane, cyclohexane, methylcyclohexane and decalin to precipitate 2,6-dimethylnaphthalene crystals,
    (C) isolating and recovering the 2,6-dimethylnaphthalene crystal precipitated in step (B) to obtain a crystal having a purity of at least 98% by weight, and a mother liquor,
    (D) distilling the mother liquor from step (C) to obtain a dimethylnaphthalene fraction by removing components having a higher boiling point than dimethylnaphthalene and components having a lower boiling point than dimethylnaphthalene, and
    (E) recycling said dimethylnaphthalene fraction in part or in whole to step (A).

2. The process according to claim 1, wherein the mixture of dimethylnaphthalene is produced from o-xylene and butadiene as starting raw materials.

3. The process according to claim 1, wherein the 2,6-dimethylnaphthalene crystal contains 0.2 to 0.6 weight % of 2,7-dimethylnaphthalene.

4. The process according to claim 1, wherein the isomerizing is carried out at a temperature of 100 to 500° C. and a weight hourly space velocity of 0.1 to 10 hours$^{-1}$.

5. The process according to claim 1, wherein the isomerizing is carried out at a temperature of 150 to 300° C. and a weight hourly space velocity of 0.2 to 5 hours$^{-1}$.

6. A multi-cyclic process for producing highly pure 2,6 dimethylnaphthalene wherein each cycle comprises:
    (A) isomerizing a mixture of dimethylnaphthalene in the presence of a catalyst selected from the group consisting of a catalyst consisting essentially of a mordenite being substantially of a hydrogen form and having a molar ratio of silica to alumina of at least 100 and a catalyst consisting essentially of a mordenite being substantially of a hydrogen form and having a molar ratio of silica to alumina of at least 100 with at least one molding aid selected from the group consisting of alumina and silica, to form an isomerization reaction product,
    (B) crystallizing 2,6-dimethylnaphthalene from the isomerization reaction product, containing at most 5% by weight of 2,7-dimethylnaphthalene, at most 3% by weight of methylnaphthalene and at most 10% by weight of trimethylnaphthalene, each based on the total amount of dimethylnaphthalene compounds contained in the isomerization reaction product formed in step (A)

in the presence of at least one solvent selected from the group consisting of hexane, heptane, octane, isooctane, nonane, methylcyclopentane, cyclohexane, methylcyclohexane and decalin to precipitate 2,6-dimethylnaphthalene crystals, (C) isolating and recovering the 2,6-dimethylnaphthalene crystals precipitated in step (B) to obtain a crystal having a purity of at least 98% by weight, and a mother liquor, (D) distilling the mother liquor from step (C) to obtain a dimethylnaphthalene fraction by removing components having a higher boiling point than dimethylnaphthalene and components having a lower boiling point than dimethylnaphthalene, and (E) recycling said dimethylnaphthalene fraction in part or in whole to step (A).

7. The process according to claim 6, wherein the mixture of dimethylnaphthalene is produced from o-xylene and butadiene as starting raw materials.

8. The process according to claim 6, wherein the 2,6-dimethylnaphthalene crystal contains 0.2 to 0.6 weight % of 2,7-dimethylnaphthalene, 0.1 to 0.4 weight % of methylnaphthalene and 0.1 to 0.2 weight % of trimethylnaphthalene.

9. The process according to claim 6, wherein the isomerizing is carried out at a temperature of 100 to 500° C. and a weight hourly space velocity of 0.1 to 10 hours$^{-1}$.

10. The process according to claim 6, wherein the isomerizing is carried out at a temperature of 150 to 300° C. and a weight hourly space velocity of 0.2 to 5 hours$^{-1}$.

* * * * *